(12) United States Patent
Brock-Fisher

(10) Patent No.: US 6,699,191 B2
(45) Date of Patent: Mar. 2, 2004

(54) ULTRASOUND DEVICE TO DETECT CAISSON'S DISEASE

(75) Inventor: George A. Brock-Fisher, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/174,316

(22) Filed: Jun. 18, 2002

(65) Prior Publication Data

US 2003/0233044 A1 Dec. 18, 2003

(51) Int. Cl.$^7$ ................................................ A61B 8/00
(52) U.S. Cl. ...................................... 600/437; 73/19.03
(58) Field of Search ........................... 600/407–471, 600/490; 367/7, 11, 130, 138; 73/620–640, 19.03; 128/916; 424/9.51, 9.52; 601/2

(56) References Cited

U.S. PATENT DOCUMENTS

| | | | |
|---|---|---|---|
| 3,622,958 A | | 11/1971 | Tucker et al. |
| 3,920,011 A | * | 11/1975 | Losee .................... 128/202.12 |
| 3,921,622 A | * | 11/1975 | Cole .......................... 600/437 |
| 4,290,432 A | * | 9/1981 | Daniels ....................... 600/437 |
| 4,319,580 A | | 3/1982 | Colley et al. ................ 128/661 |
| 4,354,502 A | | 10/1982 | Colley et al. ................ 128/663 |
| 4,689,986 A | * | 9/1987 | Carson et al. ............. 73/19.03 |
| 4,996,992 A | * | 3/1991 | LaViola et al. ............. 600/490 |
| 5,577,505 A | | 11/1996 | Brock-Fisher et al. |
| 5,632,277 A | | 5/1997 | Chapman et al. |
| 5,678,553 A | * | 10/1997 | Uhlendorf et al. .......... 600/458 |
| 5,706,819 A | | 1/1998 | Hwang et al. |
| 5,902,243 A | | 5/1999 | Holley et al. |
| 5,980,459 A | | 11/1999 | Chiao et al. |
| 6,361,510 B1 | * | 3/2002 | Zanini ............................ 601/2 |
| 6,408,679 B1 | * | 6/2002 | Kline-Schoder et al. ... 73/19.03 |

FOREIGN PATENT DOCUMENTS

WO  99/08597  2/1999

OTHER PUBLICATIONS

Christman et al, "In–Vivo Microbubble Detection in Decompression Sickness Using a Second Harmonic Resonant Bubble", Undersea Biomedical Research, vol. 13, No. 1, 1986, pp. 1–18, XP008023058.

Paulisson et al, "Evaluation Automatique Du Degre de Bulles Dans le Sang: Methodes Parametriques.\Parametric Methods for Automatic Elevational of Bubble Grade in Blood", Traitement du Signal, Montrouge, FR, vol. 9, No. 2, 1992, pp. 201–210, XP000309680.

Eftedal et al, "Detecting Intravascular Gas Bubbles in Ultrasonic Images", Medical and Biological Engineering and Computing, Peter Peregrinus Ltd. Stevenage, GB, vol. 31, No. 6, Nov. 1993, pp. 627–633, XP000415776.

* cited by examiner

*Primary Examiner*—Ali M. Imam
(74) *Attorney, Agent, or Firm*—John Vodopia

(57) ABSTRACT

An ultrasound device having a transducer propagating and receiving sound signals to/from a blood vessel of a person being examined for caisson's disease where the blood vessel is at above normal surface atmospheric pressure and a controller determining onset of the caisson's disease by analyzing the received sound signals from the transducer to determine presence of naturally occurring bubbles in the blood vessel during decompression of the blood vessel.

28 Claims, 3 Drawing Sheets

ULTRASOUND DEVICE TO DETECT CAISSON'S DISEASE

BACKGROUND OF THE INVENTION

1. Field of the Invention

The present invention relates to a device and method to detect naturally occurring gas bubbles in the bloodstream. More particularly, the present invention relates to an ultrasound device to detect caisson's disease in situations where gas bubbles are released in body tissues and fluids upon a too rapid decrease in surrounding pressure after the body's stay in a compressed atmosphere.

2. Description of the Related Art

Caisson's disease, also known as decompression sickness or "the bends", can sometimes be a fatal disorder with symptoms of neuralgic pains and paralysis, distress in breathing, and often collapse, caused by release of gas bubbles in body tissues and fluids upon a too rapid decrease in surrounding pressure after the body's stay in a compressed atmosphere. One example of caisson's disease occurrence is in underwater divers (scuba divers) because an underwater diver breathes compressed gases at above normal surface atmospheric pressure; and upon the diver's ascent, as surrounding pressure is decreased, gas bubbles can form in the diver's tissues and fluids, such as the blood stream, thereby causing caisson's disease.

For underwater divers, typically the physiological process can be described as follows: When a diver breathes gasses, such as a typical compressed air (oxygen) and nitrogen mixture, which is composed of approximately 80% nitrogen, the nitrogen dissolves into solution in the diver's blood stream as the diver dives (descends) into water. As the diver goes deeper under the water the pressure of the breathed air increases. Over time, the amount of nitrogen dissolved in the blood and other fluids increases until the amount of nitrogen reaches equilibrium with partial pressure of nitrogen in the breathed gas. Because of the higher than normal partial pressure of the nitrogen dissolved in the diver's bloodstream, if the pressure of the breathed nitrogen (gas) drops too quickly, concentration of the dissolved nitrogen in the diver's bloodstream can cause the dissolved nitrogen to come out of solution in the bloodstream in form of bubbles. The pressure of the breathed gas can drop too quickly, for example, during a rapid ascent. These bubbles typically would be small but as the bubbles come out of solution they can grow and at some point they can get to be a size sufficient to block capillaries in the blood circulatory system, thereby causing symptoms of diffuse embolisation (i.e., decompression sickness or caisson's disease).

The first manifestations (symptoms) of the caisson's disease can occur rapidly after the diver surfaces and can be characterized by joint pain, sometimes skin rash, and occasionally, cerebral central nervous system effects. Typically, the only treatment for the disease is to place the affected diver in a recompression chamber where the diver is again exposed to a higher pressure. The higher pressure forces the gas back into solution in the bloodstream and then the pressure can be released very gradually over a long period of time such that the gas does not suddenly re-evolve (come out of) solution in form of bubbles in the bloodstream.

Quickly placing a person affected by decompression sickness in a recompression chamber is critical to avoid possible permanent damage to the affected person. However, decompression sickness may have very mild manifestations or may even occur non-symptomatically. In some cases the diver may not be able to differentiate between joint pain caused by decompression sickness and joint pain caused by some other cause such as a muscle strain, a joint strain, or arthritis. Further, typically by the time symptoms manifest, controlled decompression may be too late because recompression should have already been undertaken by the time the diver starts feeling or recognizing any symptoms.

Therefore, there is a need to detect naturally occurring gas bubbles in the blood stream.

SUMMARY OF THE INVENTION

The present invention can practically and efficiently detect naturally occurring gas bubbles in a blood stream. In particular, the present invention can detect caisson's disease. For example, the device of the present invention can detect caisson's disease in a scuba diver and/or detect onset of caisson's disease in an ascending underwater diver.

The present invention can be attained by a handheld or portable ultrasound device comprising a transducer propagating and receiving sound signals to/from a blood vessel and a controller receiving the sound signals from the transducer to determine/monitor presence of naturally occurring bubbles in the blood vessel because of decompression sickness.

More particularly, the naturally occurring bubbles are free gas bubbles, such as nitrogen, helium, hydrogen, argon, and/or neon, etc. Further, the blood vessel is at a pressure above atmospheric and the controller determines/monitors presence of naturally occurring bubbles in the blood vessel during or after decompression of the scuba diver.

Further, the controller receiving the sound signals monitors formation of the naturally occurring bubbles in an underwater diver during ascent by the diver. More particularly, the controller uses a signal processing technique which is specific to the acoustic detection of bubbles, in preference to the acoustic signals arising from other sources, such as tissues or blood cells.

Further, the present invention can be attained by an ultrasound device having a transducer propagating and receiving sound signals to/from a blood vessel of a person being examined for caisson's disease where the blood vessel is at above normal surface atmospheric pressure and a controller determining onset of the caisson's disease by analyzing the received sound signals from the transducer to determine presence of naturally occurring bubbles in the blood vessel during decompression of the blood vessel.

Advantages of the invention will be set forth in part in the description which follows and, in part, will be obvious from the description, or may be learned by practice of the invention.

BRIEF DESCRIPTION OF THE DRAWINGS

The advantages of the invention will become apparent and more readily appreciated from the following description of example embodiments, taken in conjunction with the accompanying drawings of which.

DETAILED DESCRIPTION OF THE PREFERRED EMBODIMENTS

Figure 1:
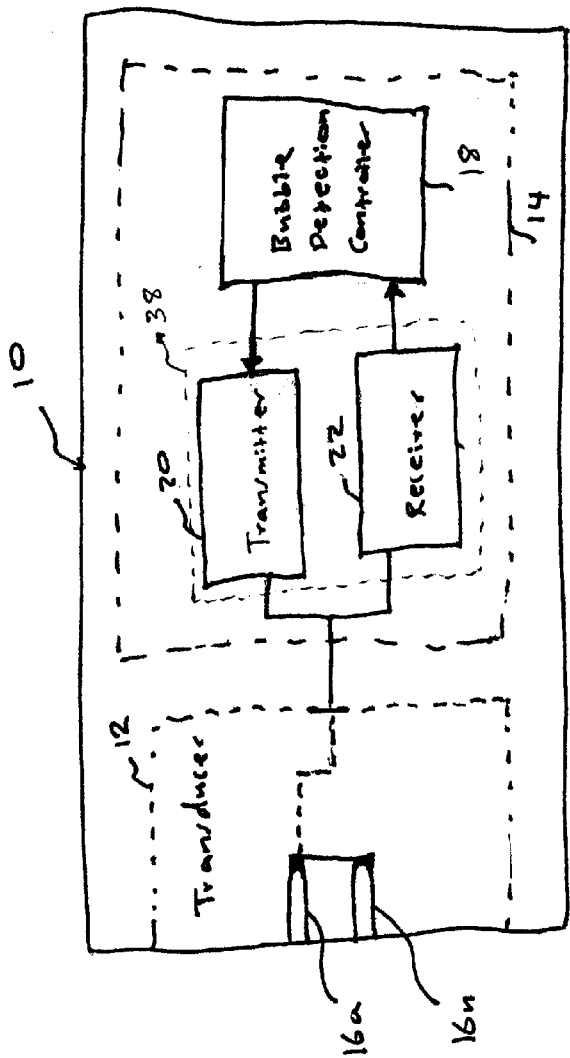
FIG. 1 is a functional block diagram of a system to detect naturally occurring bubbles in a blood stream according to the present invention.

Reference will now be made in detail to example embodiments of the present invention, which are illustrated in the accompanying drawings, wherein like reference numerals refer to the like elements throughout. The example embodiments are described below to explain the present invention by referring to the figures.

In the field of medical diagnostic ultrasound imaging, recent advances have made possible sensitive detection and imaging of encapsulated microbubbles, or bubbles of any size, in the blood stream (contrast agent imaging). An ultrasound contrast agent (UCA), such as a cardiac ultrasound contrast agent, which is typically composed of encapsulated microbubbles containing air or other gases, can be introduced into bloodstream and imaged preferentially by any number of detection techniques researched and optimized to detect UCAs (described in more detail below). In particular, UCAs can be detected and displayed on the screen preferentially over body tissues. UCA detection techniques have been developed or may be in the process of development specifically aimed at detection of UCAs, which can be in typical size ranges of caisson's disease bubbles. For example, the smallest capillaries in the blood circulatory system can be approximately 7 microns in diameter. Therefore, some typical bubbles in case of caisson's disease can be 7 microns or smaller in diameter.

The present invention is a device designed and optimized to use ultrasound contrast agent (UCA) detection techniques to detect caisson's disease by detecting presence of naturally occurring microbubbles in blood streams. In particular, the present invention can use a UCA detection technique to detect naturally occurring nitrogen gas bubbles in bloodstreams of an underwater diver. Several techniques are known in the medical ultrasound field to detect UCAs. Any conventional or future UCA detection technique can be optimized and used in the device of the present invention as follows. Typical gas filled bubbles that cause caisson's disease have sizes that would have a resonant frequency in ranges of two and three megahertz (MHz) or higher. Typical UCA detection techniques also operate at resonant frequency in ranges of one to ten megahertz. Further, as described in more detail below, some UCA detection techniques have been optimized to enhance detection of microbubbles in the bloodstream relative to tissue, which advantageously can be used to detect caisson's disease. Further, bubbles due to caisson's disease likely exist in smaller sizes before the bubbles reach a size of 7 microns, which can be a typical size of lung capillaries. The bubbles are created from some sort of cavitation nucleus, and grow as more gas dissolves out of the blood and into the bubbles. Once a bubble exists, the bubble provides an interface where the gas can dissolve out of the bloodstream and dissolve into the bubble fairly rapidly. Therefore, UCA detection techniques would be well suited to detect free or naturally occurring microbubbles in blood streams, for example, microbubbles that cause caisson's disease in case of underwater divers.

Typical UCA detection techniques detect flexible encapsulated microbubbles, which are made up of a heavy gas encapsulated in some type of a shell or coating. For example, the shell may be a thin biodegradable polymer coating, lipid coating, human albumin, cyanacrylate, sugar, or other formulations that can contain gases. The shell that encapsulates the gases prevents the gases from diffusing into bloodstream.

One technique to detect encapsulated microbubbles is second harmonics, which uses a harmonic response property of microbubble contrast agents. When an ultrasound pulse (signal, energy) is transmitted at a fundamental ultrasound frequency F0, the received response arising from linear scattering and propagation occurs at the same frequency F0. The received (echoed) ultrasound pulses will also include a second harmonic component at or about twice F0, which is 2×F0, arising from second harmonic non-linear propagation. A filter on the receiving side preferentially detects the second harmonic signals. Contrast agent bubbles can be detected because the contrast agent bubbles have a higher level (amplitude) of second harmonic component than tissue, which can also provide the second harmonic response. While the second harmonics technique improved detection of contrast agent bubbles relative to tissue or in presence of tissue reflectors, the technique only improves the preferential detection of contrast agent bubbles by about 8 decibels.

Other techniques can improve capturing the non-linearity of reflection caused by a microbubble. For example, a pulse inversion technique disclosed in U.S. Pat. No. 5,706,819, originally assigned to Advanced Technology Laboratories and now assigned to Philips Electronics, N.A. Corp. (assignee of the present application), and the contents of which is incorporated herein by reference. In the pulse inversion technique, ultrasound pulse transmits occur multiple times in pairs and each time the ultrasound pulses are transmitted into the body, wave forms (phases) of the transmitted ultrasound pulses are successively inverted. The received (echoed) ultrasound pulses, stored as data sets, are summed with succeeding received ultrasound pulses, causing linear signals to cancel out because of the inversion. However, non-linear signals arising from the second harmonic don't cancel. In fact, the second harmonic signals will tend to add because they are a second order. The pulse inversion technique can improve the contrast agent to tissue ratio (i.e., improve detection of UCAs in the presence of tissue) beyond that which is obtainable with second harmonics imaging.

Another technique to improve capturing the non-linearity of reflection caused by a microbubble is power modulation disclosed in U.S. Pat. No. 5,577,505, originally assigned to Hewlett-Packard Company and now assigned to Philips Electronics, N.A. Corp. (assignee of the present application), and the contents of which is incorporated herein by reference. The power modulation technique is similar to the pulse inversion technique except that instead of inverting the phases of the transmitted ultrasound pulse pairs, the amplitude of the ultrasound pulse pairs is changed (for example, modulated). The system gain compensates (corrects) received ultrasound pulse pairs for the amplitude changes and then the system performs a subtraction on each ultrasound pulse pair, causing the linear signals to cancel out and any non-linear signals from the target (for example, UCA) to remain. This power modulation technique also can improve the contrast agent to tissue ratio (i.e., improve detection of UCAs in the presence of tissue).

Another technique to improve capturing the non-linearity of reflection caused by a microbubble is disclosed in U.S. Pat. No. 5,632,277 (Siemens), the contents of which is incorporated herein by reference. The Siemens technique is similar to the pulse inversion technique but this technique varies carrier phases of wave forms of ultrasound pulse pairs or sequences as they are transmitted. The system processes received ultrasound pulses with a compensating phase shift and then performs a subtraction or comparison, causing the linear signals to cancel out and any non-linear signals from the target (for example, UCA) to remain. The Siemens technique also can improve the contrast agent to tissue ratio (i.e., improve detection of UCAs in the presence of tissue).

Another technique to improve capturing the non-linearity of reflection caused by a microbubble is disclosed in U.S.

Pat. No. 5,902,243 (Acuson), the contents of which is incorporated herein by reference. The Acuson technique involves modulating the phase or other components of a transmit ultrasound pulse wave form, compensating for the modification on received ultrasound pulses, and then performing a comparison operation on the ultrasound pulse pairs. The Acuson technique also can improve the contrast agent to tissue ratio (i.e., improve detection of UCAs in the presence of tissue).

Another technique to improve capturing the non-linearity of reflection caused by a microbubble is disclosed in U.S. Pat. No. 5,980,459 (General Electric), the contents of which is incorporated herein by reference. The General Electric technique transmits a set of phase-coded ultrasound pulses and uses a filtering technique corresponding to the phase-coding on received ultrasound pulses. The General Electric technique also can improve the contrast agent to tissue ratio (i.e., improve detection of UCAs in the presence of tissue).

To detect naturally occurring microbubbles in a body tissue, the present invention provides an optimized device and an optimized UCA detection technique as follows. The present invention provides optimizing UCA detection techniques to detect naturally occurring (free) microbubbles in a body tissue. Typical UCA detection techniques can be optimized to detect free gas bubbles without shells because the UCA detection techniques have already been optimized using various linear and non-linear mathematical equations based upon mathematical, physical research and analysis that use as a model a free bubble.

The shell (encapsulation) of the gas does not necessarily provide all controlling factors for the resonant frequency. For example, there are experimental UCAs without a shell, which exist as a liquid in room temperature and boil at body temperature. Such experimental UCAs are administered into the body as liquid and once in the bloodstream heat up to become a vapor, creating bubbles without a shell. However, the gas in such experimental UCAs are not nitrogen or the other gases used for underwater diving. Therefore, although the shell may serve to shift natural resonant frequency of a bubble somewhat one way or another to help in detecting the UCA, controlling factors for the resonant frequency are more dominated by characteristics of fluid in which encapsulated bubbles exist, gas inside the encapsulation and size of the encapsulated bubble. In particular, the shell's purpose is to provide an encapsulated bubble (contrast agent) that can continue to exist in blood stream to arrive at a target area in a body. In particular, typically the shell is provided to allow the bubble to exist in blood stream through lungs. For example, when using UCAs to assess cardiac conditions, a contrast agent is typically injected in a vein. Then the injected contrast agent has to travel back to the heart, then to the right side of the heart, then through the lungs and then back to the left side of the heart.

Therefore, in the present invention a UCA detection technique is optimized to detect a bubble that resonates or changes as a function of acoustic pressure in an acoustic field. In particular, detection of free gas bubbles in a body to detect caisson's disease substantially depends on the type of gas in the free bubble (e.g., nitrogen), size of the free bubble, density of fluid associated with the free bubble and compressibility of the free bubble based on ambient pressures (i.e., during ascent of the underwater diver). In particular, the present invention provides detecting formation in a blood vessel of free naturally occurring nitrogen bubbles during an underwater ascent of a diver by analyzing changes/resonations in sound signals from the blood vessel as a function of acoustic pressure, using the UCA detection techniques described above.

Further, the present invention provides an optimized device to use the optimized UCA detection technique in an ultrasound examining manner to determine or detect the presence of naturally occurring microbubbles in bloodstreams (i.e., detect microbubbles without shells). In particular, a typical ultrasound imaging device embodying the above UCA detection techniques may not be well suited and/or optimized to detect naturally occurring microbubbles in bloodstreams of an underwater diver as follows. The typical ultrasound imaging devices would be too expensive to be used to detect caisson's disease by incorporating unnecessary functions, not well suited functionality and/or omitting critical functions. Further, the typical ultrasound imaging devices are not portable by being too large, not handheld, and not optimized for use in underwater diving scenarios, such as shipboard operations, harsh weather and/or environmental conditions (e.g., water resistant and/or proof). Therefore, the present invention provides a miniaturized (for example, by using mobile processor technology), ruggedized, and waterproof free gas bubble detector to provide warning of formation of free gas bubbles in body tissue during underwater ascent.

FIG. 1 is a functional block diagram of a microbubble detection system 10 according to the present invention, which comprises an ultrasound transducer (probe) assembly 12 and a microbubble detector 14. The transducer 12 further comprises one or more transducer elements 16a–16n. The transducer elements 16 can be conventional transducer elements, such as piezoelectric, directional, magnetostrictive, or other available transducer elements. Each transducer element 16 is an ultrasonic transducer converting electricity to sound and converting sound to electricity. The transducer elements 16 convert electrical signals into sounds, which are propagated, for example, into tissue of a human body and reflected from internal body structures. The transducer elements 16 convert the reflected sounds back to electrical signals and the electrical signals are transmitted to the microbubble detector 14. The microbubble detector 14 processes electrical signals received from the transducer elements 16 according to a microbubble detection technique implemented in hardware/software by a bubble detection controller 18 to inform (notify) a user of caisson's disease onset. For example, an underwater diver during ascent can be informed that microbubbles are starting to form, providing the diver critical early warning to quickly seek controlled decompression or other action (as the case may be).

In an example embodiment, a single directional piezoelectric transducer element 16a is provided to perform electrical to acoustic and acoustic to electrical conversion. A single channel ultrasound transmitter 20 is coupled to the single directional piezoelectric transducer element 16a and to the bubble detection controller 18. An ultrasonic receiver 22 is connected to the same direction piezoelectric transducer element 16a and to the bubble detection controller 18. In another exemplary embodiment the transducer 12 has two directional piezoelectric transducer elements 16a and 16b to transmit and receive, respectively. In operation, both transducer elements 16a and 16b would be aimed and focused at same spot and space. The elements 16 can be directional to provide directivity so that a user can also detect presence of a blood vessel to target for examination.

A typical ultrasound transducer, such as a phased-array or other array transducer, has many transducer elements (e.g., 64 up to 288 elements) that perform electrical to acoustic and acoustic to electrical conversion and can accommodate real-time imaging based upon received electrical signals.

Therefore, in the present invention one and/or two directional transducer elements 16 with single channel transmitter 20 and receiver 22 advantageously provide directivity as well as substantially reduce the size of the transducer 12, accommodating portability and/or a handheld system 10. Of course, a phased-array transducer with corresponding transmitters/receivers, providing additional functions, such as focusing, can also be used in the present invention.

The system 10 can embody conventional UCA techniques as implemented in hardware and/or software. The system 10 can be handheld. In an example embodiment the system 10 is miniaturized to size of a pocket flashlight, a fountain pen, a wristwatch or incorporate into other diving instruments for very easy and very portable use. Further, in another example embodiment the system 10 is water proof (tight) and pressure tight so that the system 10 can be continuously carried (worn) by a diver during underwater diving.

Figure 2:
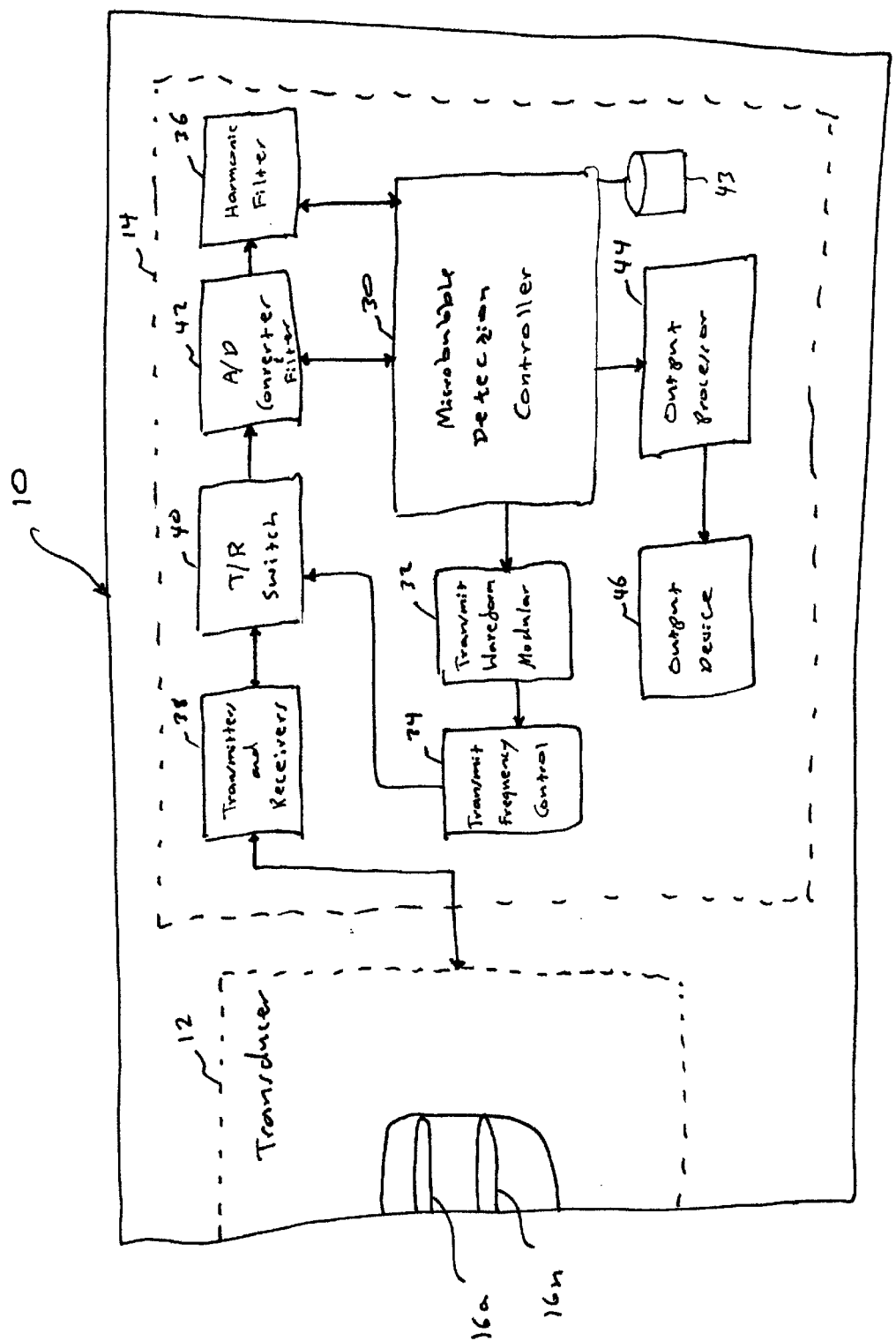
FIG. 2, is a functional block diagram of a microbubble detector according to the present invention.

FIG. 2, is a more detailed functional block diagram of an example microbubble detector 14 according to the present invention. The detector 14 incorporating conventional medical ultrasound imaging technology does not necessarily illustrate every component, emphasis instead being placed upon the components according and/or relevant to the present invention. The microbubble detector 14 comprises a microbubble detection controller 30 that performs microbubble detection techniques to detect onset of naturally occurring gas bubbles in body tissue. For example, the detection controller 30 can implement in hardware and/or software a typical ultrasound contrast imaging technique to detect naturally occurring gas bubbles. In particular, controller 30 can detect in the blood vessel free naturally occurring gas bubbles during an underwater ascent of a diver by analyzing changes/resonations in the sound signals as a function of acoustic pressure according to an optimized UCA detection technique. The detection controller 30 can implement in hardware and/or software conventional or future optimized UCA detection techniques, which improve bubble to tissue ratio (i.e., improve detection of bubbles in presence of tissue) to detect the naturally (free) occurring gas bubbles in blood vessels, such as microbubbles formed in underwater divers during ascent. In case of detecting naturally occurring microbubbles in an underwater diver, a UCA detection technique implemented by the detection controller 30 can detect microbubbles containing nitrogen, or other non-air gas mixtures used in air-non-air mixtures for scuba diving, such as helium (heliox), hydrogen, argon, neon and/or trimix. For example, an oxygen-helium mixture is typically used in deep diving situations.

On the transmit side, a transmit waveform modulator 32 and a transmit frequency control 34, under control of the microbubble detection controller 30, set the transmit frequency of the transmit signals and modulate the various transmitted signal lines, respectively. For example, the detection controller 30 controls transmit signals according to the microbubble detection technique used to detect naturally occurring microbubbles in the body tissue, such as second harmonics, pulse inversion, power modulation or other techniques. The controller 30 can transmit signals, via transmit frequency control 34 and transmit waveform modulator 32, along same line of sight or same angular direction to have characteristics of transmit modulation required by the microbubble detection technique implemented in the controller 30.

On the receive side, an A/D converter and filter 42, under control of the microbubble detection controller 30, converts analog signals received from the transducer 12 into digital signals and uses a digital filter (e.g., an RF filter) to filter signals outside the desired receive band from the received data. In particular, the A/D converter and filter 42 provides a pre-amplifier with a variable gain stage to control level of signals coming back and a filter to select frequency range of interest. Alternatively, successive samples, each corresponding to a single firing of the transmitter 20 (transmitters and receivers 38), can be stored in memory 43 and automatically read from memory 43 to be combined according to a combination operation. The combination operation could include arithmetic additions, subtraction or other combinational techniques to provide bubble information to the detection controller 30.

In case of using a second harmonics microbubble detection technique, a harmonic filter 36 filters out second harmonic preferentially and provides the second harmonic to the controller 30 for bubble presence analysis. Alternatively, it may be preferential to employ the harmonic filter 36 as an analog filter ahead of the A/D converter and filter 42. Therefore, the present invention provides a device that uses a non-linear bubble detection technique to detect the presence of naturally occurring microbubbles in bloodstream of an underwater diver during the diver's ascent (i.e., detect blood stream microbubbles caused by caisson's disease).

Transmitters and receivers 38 in communication with the transducer 12 transmit and receive, respectively, electrical information signals to/from the transducer 12. A T/R switch 40 can place the transmitter and receivers 30 in a transmit or receive mode, thereby placing the transducer 12 in a transmit or receive mode. The T/R switch 40 provides the A/D converter and filter 42 the analog signals received from the transducer assembly 12.

An output processor 44 processes information output from the microbubble detection controller 30 to output the information to an output device 46. The output device 46 can be, for example, a display, an audio device or vibrating mechanism that vibrates the system 10, to warn/alert a user of caisson's disease onset visually, audibly (e.g., via an alarm), or by vibration.

Although, the example embodiment illustrates an integrated interface between the transducer 12 and the microbubble detector 14, the present invention is not limited to such embodiment. For example, a non-integrated interface between the transducer 12 and microbubble detector 14 can be provided as follows. The transducer 12 and the microbubble detector 14 can interface via conductor elements (not shown), such as conventional wires (cable) that exchange electrical signals between the transducer 12 and microbubble detector 14. Therefore, wires can provide a mechanism to connect the transducer 12 to the microbubble detector 14 using conventional interface technology. Other conventional interface technology, such as wireless, can interface transducer 12 with detector 14. A remote detector 14 can be implemented, for example, in a handheld, laptop or desktop computer. The non-integrated interface can accommodate wearing of the system 10 by a diver to detect onset of caisson's disease real-time underwater and during the diver's ascent. For example, probe 12 could be laid flat on a diver's skin in a location that would not tend to be disturbed by the diver's motion and aimed towards a target blood vessel, such as femoral artery in groin, popliteal on back of knee, brachial artery in arm or carotids in neck. The diver locally or an operator remotely, for example, on an above water location (as the case may be), interfaces with detector 14, which is located locally with the diver or remotely to the diver, respectively, to control probe 12 to detect onset of caisson's disease in the diver either during underwater ascent or after the diver surfaces. If caisson's disease is detected, appropriate action can be taken, such as controlled decompression in a compression chamber.

Although the exemplary embodiment describes an integrated output device 44, the present invention is not limited to such implementation. Another example embodiment can provide an external output device 44 as follows. The output device 44 can be remote, for example, a handheld or laptop computer, and in communication with the system 10 via conventional communication technologies, such as wire and wireless. In case of an ascending underwater diver, advance warning can be provided to personnel above water or on land (e.g., on a ship, a diving location offshore or onshore) regarding caisson's disease onset, so that the personnel can begin recompression chamber preparation.

In another example embodiment, the transducer 12 further comprises a directional narrow beam transducer element 16c. The transducer element 16c is steered into a blood pool where naturally occurring microbubbles can be detected. The microbubble detection controller 30 further provides a separate operational mode using Continuous Wave (CW) Doppler to help locate a blood vessel. The transmitters and receivers 38 would provide the transducer element 16c a continuous signal in the CW Doppler mode. In an alternative embodiment, one of the two transducer elements 16a and 16b can also be used in the CW Doppler mode instead of providing the additional transducer element 16c.

In particular, a CW Doppler technique can be used to assist locating the beam of transducer element 16b on a blood vessel. A typical Doppler technique transmits ultrasound into a body and into a target blood vessel to measure velocity of blood flow in the blood vessel. The ultrasound scatters off of red blood cells, which are moving. The motion of the red blood cells cause reflected ultrasound to have a frequency characteristic shifted by Doppler shift. The Doppler shift is related to velocity of sound and to velocity of the blood cells. The Doppler shift can be measured, demodulated and presented as an audio sound. The Doppler shift can be used to measure/quantify the motion of blood in the vessel, thereby assisting in locating an appropriate target blood vessel for detecting naturally occurring microbubbles.

Locating a blood vessel can avoid using the system 10 to interrogate a region of body tissue or muscle that does not contain sufficiently large blood supply to be a reasonable target for detecting naturally occurring microbubbles. For example, a CW Doppler technique that provides an audio signal can be used to locate a blood vessel, such as a femoral artery, brachial artery or some other large vessel, providing a significant blood pool to provide an accurate assessment of presence of naturally occurring microbubbles.

Figure 3:
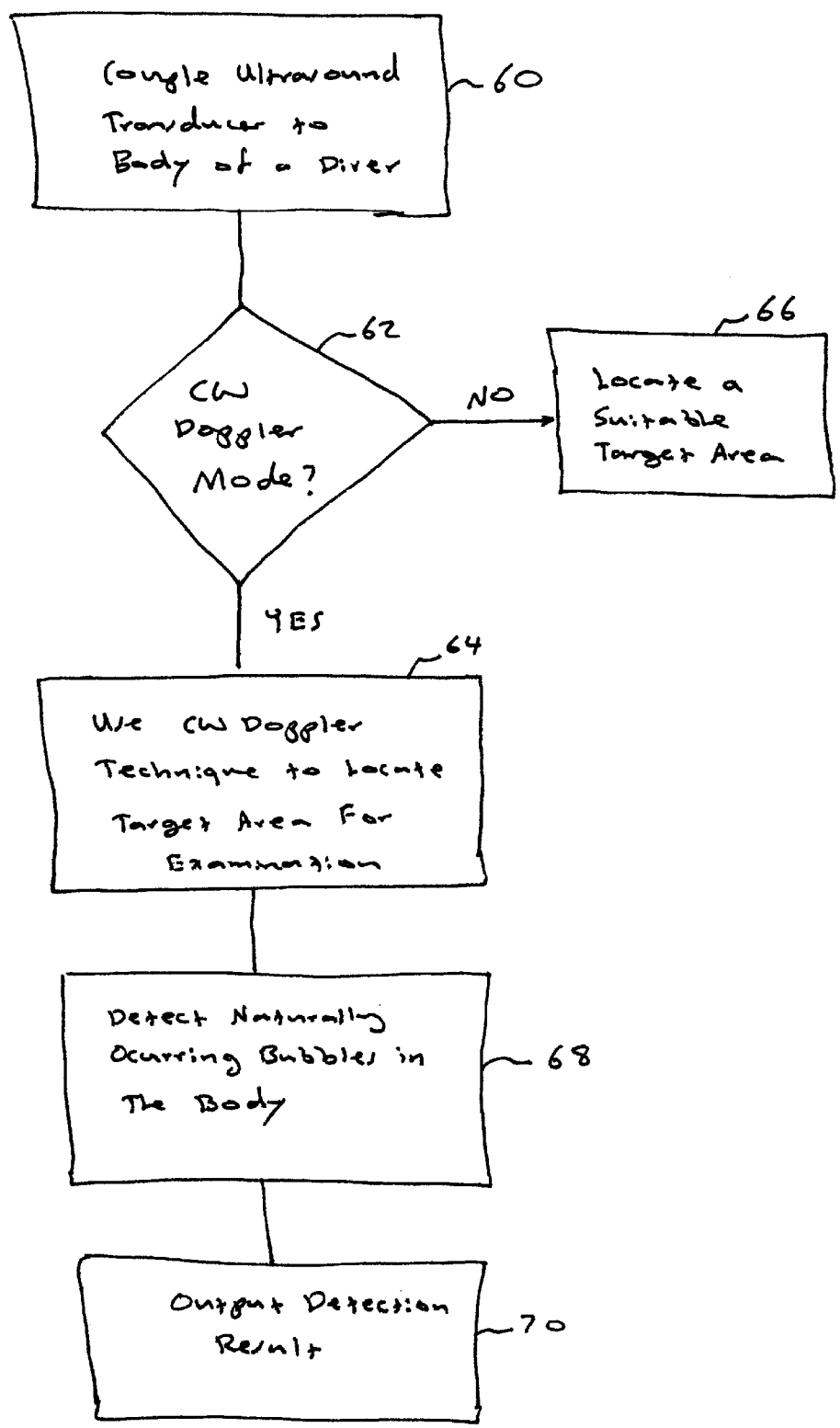
FIG. 3 is a flow chart of a method to detect bubbles in a blood stream according to the present invention.

FIG. 3 is a flow chart of a method to detect bubbles in a blood stream according to the present invention. At 60, an operator acoustically couples transducers 16 to body of a diver undergoing examination. If at 62, system 10 has a CW Doppler mode, at 64 the operator uses the CW Doppler mode to locate a target body area for caisson's disease examination, such as a desirable blood vessel in the diver's body. In particular, at 62 the CW Doppler mode can provide information, such as visual or audio signals, or selection options, to the operator to determine/locate and/or select the desirable blood vessel.

If at 62, system 10 does not have a CW Doppler mode or the operator foregoes the CW Doppler mode, at 66 the operator can locate a suitable site in the body for examination, which can be the femoral or popliteal artery in field of view. At 66, the operator causes the system 10 to commence an exam sequence to detect formation and/or presence of microbubbles in the body (i.e., detect onset of caisson's disease). In particular, at 66, the exam sequence would alternately or simultaneously transmit into and receive ultrasound signals to/from the target area selected at 64 or 66 via transmitters and receivers 38 under control of microbubble detection controller 30. At 66, the microbubble detection controller 30 executes an optimized UCA detection technique, as implemented in hardware and/or software, to analyze returned acoustic signals from the body to determine if any free naturally occurring microbubbles (bubbles of any size as required/specified) made up of gases breathed by the diver underwater (e.g., nitrogen) are present in the diver's body tissue, such as blood streams.

More particularly, in case the microbubble detector 14 provides a CW Doppler mode, at 64 the operator can place the detector 14 in a CW Doppler mode and then adjust orientation of probe 12 until transducer element(s) 16 receive a strong signal according to the CW Doppler technique, which can indicate that the ultrasound beam is focused in a blood pool region. Then the operator could switch the detector 14 from the CW Doppler operation mode to a contrast agent mode operation mode or intermittently the detector 14 could operate in a contrast detection mode, to provide an estimate of amount of microbubbles present in the blood pool region.

At 68, in the contrast detection mode, the controller 30 controls firing pulses, receiving echoes of the pulses, analyzing the echoes according to any of the known bubble detection techniques as optimized to detect bubbles made up of gases breathed by an underwater diver, including as optimized to detect bubbles while the diver is underwater and during ascent, and determining a signal representing presence of the bubbles.

At 70, the microbubble detection controller 30 outputs analysis results based upon the received acoustic signals from the body. For example, presence of bubbles can be indicated via an alarm (audio or vibratory) or visual display of information. Further, bubble presence can be indicated as a confidence score/measure based upon bubble-to-tissue signal ratios determined at 68 by the controller 30 according to one of the implemented UCA detection technique. The confidence score can be based upon a predefined target threshold according to sensitivity and/or specificity, for example, according to industry (e.g., medical industry) and/or government standards.

An example ultrasound device of the present invention has a transducer 12 propagating and receiving via two directional piezoelectric transducer elements 16 sound signals to/from a blood vessel and a controller 30 receiving the sound signals from the transducer elements 16 to determine presence of free naturally occurring bubbles in the blood vessel. In particular, the blood vessel can be at a pressure above atmospheric and the controller 30 determines the presence of the naturally occurring bubbles in the blood vessel during decompression of the blood vessel. The naturally occurring bubbles are made up of gases breathed by a diver at the pressure above atmospheric (for example, underwater), such as nitrogen gas.

The controller 30 can perform CW Doppler interrogation to facilitate placement of the blood vessel in an ultrasound beam emitted from the transducer elements 16. The controller 30 performs bubble detection techniques to determine presence of the naturally occurring bubbles. In particular, the controller 30 can use a known UCA detection technique as optimized according to known UCA detection techniques to detect the naturally occurring bubbles. The UCA detection technique used by the controller 30 can arrive at a measure of bubble signals preferentially, to substantial exclusion of tissue signals. Such UCA detections techniques can include second harmonic imaging, pulse inversion imaging, power modulation imaging, or any other technique shown to improve bubble-to-tissue signal ratios. The controller 30 can provide a confidence indication based on measuring ratio of bubble signals to tissue signals.

According to the present invention, device 10 is built portable, such as size of a suitcase, a notebook computer, or built handheld, such as size of a ballpoint pen. In another example embodiment, the device 10 can be made waterproof and miniaturized using, for example, mobile processor technology, to be worn continuously by a diver operating underwater. The device 10 could provide an audible, visual or vibratory alarm that bubbles are forming during the diver's ascent.

Although a few example embodiments of the present invention have been shown and described, it would be appreciated by those skilled in the art that changes may be made in the embodiments without departing from the principles and spirit of the invention, the scope of which is defined in the claims and their equivalents.

What is claimed is:

1. An ultrasound device, comprising:

a waterproof housing, an acoustic transducer arranged in the housing to transmit and receive sound signals to/from a blood vessel of a person being examined for caisson's disease while the person is underwater; and a processor coupled to the transducer and programmed to a determine onset of the caisson's disease by analyzing returned sound signals from the blood vessel to detect in the blood vessel free naturally occurring gas bubbles.

2. The ultrasound device according to claim 1, wherein the processor analyzes changes/resonation in the returned sound signals according to an ultrasound contrast agent detection technique.

3. The ultrasound device according to claim 1, wherein the transducer and the processor are miniature, such that the device is the size of a ballpoint pen.

4. The ultrasound device according to claim 1, wherein the transducer and the processor are miniature, such that the device is the size of a flashlight.

5. The ultrasound device according to claim 1, wherein the processor is in a handheld computer and coupled to the transducer via a wire.

6. The ultrasound device according to claim 1, wherein the transducer is miniature such that the transducer is the size of a ballpoint pen and the processor is a handheld or laptop computer wirelessly coupled to the transducer.

7. The ultrasound device according to claim 6, wherein the transducer is miniature to be fastened at the groin, arm, neck or back of knee of the person.

8. The ultrasound device according to claim 1, wherein the transducer transmits and receives continuous wave sound signals to/from the body of the person and the processor is further programmed to locate the blood vessel in the body according to a Doppler technique based on the received continuous wave sound signals.

9. The ultrasound device according to claim 1, wherein the housing includes a mechanism for enabling the housing to be continuously carried or worn by or fastened to the person during movement underwater.

10. An ultrasound device, comprising:

a waterproof housing, a transducer arranged in the housing to propagate and receive sound signals to/from a blood vessel at above normal surface atmospheric pressure while the person is underwater; and a controller receiving the sound signals from the transducer to determine a presence of naturally occurring bubbles in the blood vessel during decompression of the blood vessel.

11. The ultrasound device of claim 10, wherein the naturally occurring bubbles are made up of gases breathed by an underwater diver.

12. The ultrasound device of claim 11, wherein the gases are a gas mixture of oxygen and at least one of nitrogen, helium, hydrogen, argon, neon, or other gases breathed by the underwater diver.

13. The ultrasound device of claim 12, wherein the controller determines the presence of the naturally occurring bubbles according to a sound signal processing technique, which, based upon the received acoustic signals, performs acoustic detection of bubbles in preference to the received acoustic signals arising from other sources, such as tissues or blood cells.

14. The ultrasound device according to claim 10, wherein the transducer propagates and receives continuous wave sound signals to/from a body of a person and the controller receives the continuous wave sound signals to perform Doppler techniques locating the blood vessel in the person.

15. The ultrasound device according to claim 10, wherein the controller determines the presence of the naturally occurring bubbles by analyzing the received sound signals according to an ultrasound contrast agent detection technique optimized to detect a bubble that resonates or changes as a function of acoustic pressure in an acoustic field.

16. The ultrasound device according to claim 10, wherein the housing includes a mechanism for enabling the housing to be continuously carried or worn by or fastened to the person during movement underwater.

17. A method for determining onset of caisson's disease in a person located underwater, comprising:

locating a blood vessel in a body of the person to be examined for caisson's disease;

fastening a single ultrasound transducer to the body such that the ultrasound transducer is continuously carried or worn by the person during underwater movement;

aiming a steering beam of thie fastened ultrasound transducer towards the located blood vessel;

propagating and receiving ultrasound signals to/from the located blood vessel while underwater;

detecting naturally occurring bubbles in the located blood vessel while the body ascends underwater; and determining an onset of caisson's disease in the person based upon the detection of naturally occurring bubbles in the located blood vessel.

18. The method according to claim 17, further comprising analyzing changes/resonations in the ultrasound signals received from the located blood vessel as a function of acoustic pressure to detect the naturally occurring bubbles.

19. The method according to claim 18, wherein the person while underwater breathes a gas mixture of oxygen and at least one of nitrogen, helium, hydrogen, argon, neon, or other gases to be breathed by the person and the naturally occurring bubbles are bubbles made up of such gases.

20. The method according to claim 19, wherein the changes/resonation in the ultrasound signals are analyzed according to an optimized ultrasound contrast agent detection technique.

21. The method according to claim 17, wherein the step of locating the blood vessel comprises the step of propagating and receiving continuous wave ultrasound signals into the located blood vessel and analyzing the received continuous wave signals according to a Doppler technique to locate the blood vessel.

22. The method according to claim 17, further comprising providing a warning to the person while underwater when the onset of caisson's disease is determined to thereby enable the person to counter the onset of caisson's disease.

23. The method according to claim 17, further comprising activating an audio device to generate sound when the onset of caisson's disease is determined to alert the person thereby enable the person to counter the onset of caisson's disease.

24. The method according to claim 17, further comprising activating a vibrating mechanism to vibrate the ultrasonic transducer when the onset of caisson's disease is determined to alert the person and enable the person to counter the onset of caisson's disease.

25. The method according to claim 17, further comprising displaying an indication of the onset of caisson's disease when the onset of caisson's disease is determined to alert the person and enable the person to counter the onset of caisson's disease.

26. An ultrasound device, comprising:
a waterproof housing;
an acoustic transducer arranged in the housing to transmit and receive sound signals, including continuous wave sound signals, to/from blood pool regions in a person being examined for caisson's disease while the person is underwater; and
a processor coupled to the transducer and programmed to locate the blood pool regions in the body according to a Doppler technique based on the received continuous wave sound signals, to intermittently, while locating the blood pool regions, determine an onset of the caisson's disease by analyzing returned sound signals from the located blood pool regions to provide an estimate amount of free naturally occurring gas bubbles in the located blood pool regions.

27. The ultrasound device according to claim 26, wherein the naturally occurring bubbles are made up of gases breathed by the person underwater and the gases are a gas mixture of oxygen and at least one of nitrogen, helium, hydrogen, argon, neon, or other gases to be breathed by the person underwater.

28. The ultrasound device according to claim 26, wherein the housing includes a mechanism for enabling the housing to be continuously carried or worn by or fastened to the person during movement underwater.

\* \* \* \* \*